United States Patent [19]

Johnson et al.

[11] Patent Number: 4,919,753

[45] Date of Patent: Apr. 24, 1990

[54] NONWOVEN FABRIC-LIKE PRODUCT USING A BACTERIAL CELLULOSE BINDER AND METHOD FOR ITS PREPARATION

[75] Inventors: Donald C. Johnson, Auburn; Amar N. Neogi, Seattle, both of Wash.

[73] Assignee: Weyerhaeuser Company, Tacoma, Wash.

[21] Appl. No.: 299,691

[22] Filed: Jan. 23, 1989

Related U.S. Application Data

[63] Continuation of Ser. No. 849,982, Apr. 10, 1986, abandoned.

[51] Int. Cl.$^5$ .............................................. D21H 5/12
[52] U.S. Cl. ..................... 162/116; 162/145; 162/146; 162/148
[58] Field of Search ............... 162/91, 100, 99, 109, 162/116, 158, 157.1, 142, 141, 146, 149, 148, 150, 145; 435/101, 823

[56] References Cited

U.S. PATENT DOCUMENTS

| | | | |
|---|---|---|---|
| 2,026,253 | 12/1935 | Sanborn | 162/158 |
| 3,350,260 | 10/1967 | Johnson | 162/116 |
| 4,070,235 | 1/1978 | Marshall | 162/116 |
| 4,320,198 | 3/1982 | Mynatt | 162/99 |
| 4,588,400 | 5/1986 | Ring et al. | 604/304 |
| 4,655,758 | 4/1987 | Ring et al. | 162/100 |

FOREIGN PATENT DOCUMENTS

51-11902  1/1976  Japan ................................ 162/148

OTHER PUBLICATIONS

Casey, *Pulp and Paper*, 3rd ed. (1980), vol. II, p. 1130.

*Primary Examiner*—Peter Chin

[57] ABSTRACT

The present invention is a method of bonding a fibrous wet laid nonwoven fabric-like product using bacterial cellulose as a binder. The bacterial cellulose most useful for the invention is the type formed in an agitated culture. Microorganisms of the genus Acetobacter which are genetically adapted to be good cellulose producers under agitated conditions are preferred cellulose producers. From 1–30% of the bacterial cellulose may be added to a water slurry of other sheet forming fibers as a binder. Preferably 20% or less bacterial cellulose is used since higher amounts retard drainage rates significantly. Bacterial cellulose conveys many desirable properties such as excellent hydrophilicity with low air porosity and high tensile index. It may be used in many cases as a total replacement for the latex binders now used for manufacture of nonwoven fabrics. Bacterial cellulose is especially well adapted for the manufacture of pattern bonded sheets.

20 Claims, 3 Drawing Sheets

NONWOVEN FABRIC-LIKE PRODUCT USING A BACTERIAL CELLULOSE BINDER AND METHOD FOR ITS PREPARATION

This is a continuation of application Ser. No. 06/849,982, filed Apr. 10, 1986 abandoned.

BACKGROUND OF THE INVENTION

The present invention is a method of making a nonwoven fabric-like product using bacterially formed cellulose as a binding agent. The invention further includes the wet formed products made by the above method. A particularly useful bacterial cellulose is one formed in aerated agitated culture using a microorganism of the genus Acetobacter genetically selected for cellulose production under agitated conditions.

It has been known for many years that cellulose can be synthesized by certain bacteria, particularly those of the genus Acetobacter. This phenomenon has received considerable study in the years following 1930. While a great deal has been learned about the production of bacterial cellulose in the past 50 years, it has been primarily of academic interest and only very recently has it been proposed for use in products having potential commercial significance.

Taxonomists have been unable to agree upon a consistent classification of the cellulose producing species of Acetobacter. For example, the cellulose producing microorganisms listed in the 15th Edition of the Catalog of the American Type Culture Collection under accession numbers 10245, 10821, and 23769 are classified both as *Acetobacter aceti subsp. xylinum* and as *Acetobacter pasteurianus*. For the purposes of the present invention any species or variety of bacterium within the genus Acetobacter that will produce cellulose under agitated conditions should be regarded as a suitable cellulose producer for the purposes of the present invention.

*Acetobacter aceti subsp. xylinum*, for purposes of brevity hereafter referred to simply as *Acetobacter xylinum*, is normally cultured under static conditions with the cellulose microfibrils being produced at the air medium interface. Most bacteria of this species are very poor cellulose producers when grown in agitated culture. Various reasons have been proposed to account for this phenomenon. It may be that agitated culture induces a tendency to mutation to noncellulose producing types. Perhaps for this reason two recent proposed products using bacterial cellulose have been based on static cultures of *Acetobacter xylinum*.

Brown, in U.S. Pat. No. 4,378,431, describes a method for imparting hydrophilic characteristics to fibrous hydrophobic substances. The Acetobacter bacterium is cultured in the presence of the synthetic substrate. During the culture process, cellulose microfibrils are produced on and around the surface of the substrate. The substrate is preferably in the form of a fiber which may be either woven or nonwoven. Natural substrates may also be used. The inventor notes, without providing an example, that the strength of paper may be increased. The product is seen as a combination of a bacterial pellicle and the substrate. To the present inventors' knowledge this process has not had any commercial utilization due to several problems. A major one is that the substrate must be retained in the culture medium for a long enough period of time for cellulose to grow on the surface. For most proposed applications further treatment, such as a hot caustic leaching, would then be necessary to remove the residual bacteria before use. Such a treatment could seriously damage the integrity of the substrate.

U.K. Patent application 2,131,701A describes formation of bacterial pellicle which is ultimately said to be usable as a wound dressing. This process also employs static culture conditions for formation of the cellulose pellicle.

In our earlier U.S. patent application, Ser. No. 788,915, filed Oct. 18, 1985, we disclose Acetobacter varieties which are vigorous cellulose producers under agitated culture conditions. The cellulose produced by the microorganisms and culture conditions disclosed in this application appears to be a unique type, physically quite different from the bacterial cellulose produced in static cultures. It has a highly branched, three dimensional, reticulated structure. A normal cellulose pellicle produced in static culture tends to have a lamellar structure with a very much lower amount of branching. This application claims sheets formed from the bacterial cellulose. These sheets are unique in their very low air porosity and high resistance to densification by conventional means.

The present invention is not directed to sheet materials in which bacterial cellulose is a major component. Rather, it is directed to the use of bacterial cellulose as a minor component used as a binder for other fibers in wet formed sheets.

SUMMARY OF THE INVENTION

The present invention comprises a method for bonding a fibrous wet laid, nonwoven paper or fabric-like product using bacterial cellulose as the binder. The bacterial cellulose is present as a minor portion of the total components of the ultimate product. Normally it will be used within a range of 1–30% by weight of the product. More preferably, it is present in an amount of about 2–20% by weight of the product. Larger amounts of bacterial cellulose result in sheet making slurries which have inordinately long drainage times.

The invention is further directed to the nonwoven paper or fabric-like products formed by the above method.

The term "bacterial cellulose" as used herein refers to a product free of residual bacterial cells made under agitated culture conditions by a bacterium of the genus Acetobacter. The strains of bacteria employed and the culturing conditions used may be similar to those disclosed in our earlier application, Ser. No. 788,915.

The method is suitable for use with virtually any fiber which can be formed into a sheet by a wet process. These fibers may be of either hydrophobic or hydrophilic nature and may be of natural or synthetic origin. Suitable fibers may be based on cellulose, polyester, polyolefin, nylon, acrylic, glass, and metallic materials. Among the cellulose fibers suitable are materials such as wood pulps, which may be of either softwood or hardwood origin. The fibers may be purified by any of the well known processes. These include but are not limited to the well known mechanical, thermomechanical, kraft and sulfite pulping methods. The cellulose fibers may also be of chemically or physically modified nature such as viscose, acetate, or cuprammonium rayons. The polyolefins would include materials made from polyethylene or polypropylene, the latter presently being the more important material.

An apparent unique property of bacterial cellulose is its ability to form pattern bonded sheets. In a pattern bonded sheet some overall bonding occurs. However, the most intense bonding of the major fiber constituents occurs in some predetermined geometric pattern. Pattern bonded nonwoven sheet materials, bonded with synthetic resins, are well known in the prior art. To the present inventors' knowledge, this has not been accomplished before using a cellulose binder with other types of fibers in situ. A preferred way of making pattern bonded materials is the use of a geometrically patterned mask overlying the drainage wire on which the sheets are formed. A forming screen made in some predetermined pattern is also suitable.

It is an object of the present invention to provide a method for making wet laid nonwoven paper or fabric-like products using bacterial cellulose as a binder material.

It is a further object to provide new nonwoven paper or fabric-like products having unique physical properties.

These and many other objects will become readily apparent on reading the following detailed description taken in conjunction with the attached drawings.

DESCRIPTION OF THE PREFERRED EMBODIMENTS

The procedures of the present invention are best understood by reference to the following examples.

EXAMPLE 1

Production of Bacterial Cellulose

The bacterial cellulose of the present invention was produced in agitated culture by a strain of *Acetobacter aceti* var. *xylinum* grown as a subculture of ATCC Accession No. 53-263, Deposited Sept. 13, 1985 under the terms of the Budapest Treaty.

The following base medium was used for all cultures. This will be referred to henceforth as CSL medium.

| Ingredient | Final Conc. (mM) |
|---|---|
| $(NH_4)_2SO_4$ | 25 |
| $KH_2PO_4$ | 7.3 |
| $MgSO_4$ | 1.0 |
| $FeSO_4$ | 0.013 |
| $CaCl_2$ | 0.10 |
| $Na_2MoO_4$ | 0.001 |
| $ZnSO_4$ | 0.006 |
| $MnSO_4$ | 0.006 |
| $CuSO_4$ | 0.0002 |
| Vitamin mix | 10 mL/L |
| Carbon source | As later specified |
| Corn steep liquor | As later specified |
| Antifoam | 0.01% v/v |

The final pH of the medium was 5.0 ± 0.2.
The vitamin mix was formulated as follows:

| Ingredient | Conc. mg/L |
|---|---|
| Inositol | 200 |
| Niacin | 40 |
| Pyridoxine HCl | 40 |
| Thiamine HCl | 40 |
| Ca Pantothenate | 20 |
| Riboflavin | 20 |
| p-Aminobenzoic acid | 20 |
| Folic acid | 0.2 |
| Biotin | 0.2 |

Corn steep liquor (CSL) varies in composition depending on the supplier and mode of treatment. A product obtained as Lot E804 from Corn Products Unit, CPC North America, Stockton, Calif. may be considered typical and is described as follows:

| Major Component | % |
|---|---|
| Solids | 43.8 |
| Crude protein | 18.4 |
| Fat | 0.5 |
| Crude fiber | 0.1 |
| Ash | 6.9 |
| Calcium | 0.02 |
| Phosphorus | 1.3 |
| Nitrogen-free extract | 17.8 |
| Non-protein nitrogen | 1.4 |
| NaCl | 0.5 |
| Potassium | 1.8 |
| Reducing sugars(as dextrose) | 2.9 |
| Starch | 1.6 |

The pH of the above is about 4.5.

The bacteria were first multiplied as a pre-seed culture using CSL medium with 4% (w/v) glucose as the carbon source and 5% (w/v) CSL. Cultures were grown in 100 mL of the medium in a 750 mL Falcon #3028 tissue culture flask at 30° C. for 48 hours. The entire contents of the culture flask was blended and used to make a 5% (v/v) inoculum of the seed culture. Preseeds were streaked on culture plates to check for homogeneity and possible contamination.

Seed cultures were grown in 400 mL of the above-described medium in 2 L baffled flasks in a reciprocal shaker at 125 rpm at 30° C. for two days. Seed cultures were blended and streaked as before to check for contamination before further use.

Bacterially formed cellulose for the work to be described later was formed in a continuously stirred 14 L Chemap fermentor using an initial 12 L culture volume inoculated with 5% (v/v) of the seed cultures. An initial glucose concentration of 32 g/L in the medium was supplemented during the 72-hour fermentor run with an additional 143 g/L added intermittently during the run. In similar fashion, the initial 2% (v/v) CSL concentration was augmented by the addition of an amount equivalent to 2% by volume of the initial volume at 32 hours and 59 hours. Cellulose concentration reached about 12.7 g/L during the fermentation. Throughout the fermentation dissolved oxygen was maintained at about 30% air saturation.

Following fermentation, the cellulose was allowed to settle and the supernatant liquid poured off. The remaining cellulose was washed with deionized water and then extracted with 0.5M NaOH solution at 60° C. for 2 hours. After extraction the cellulose was again washed with deionized water to remove residual alkali and bacterial cells. More recent work has shown that 0.1M NaOH solution is entirely adequate for the extraction step. The purified cellulose was maintained in wet condition for further use. This material was readily dispersible in water to form a uniform slurry.

The bacterial cellulose produced under stirred or agitated conditions, as described above, has a microstructure quite different from that produced in conventional static cultures. It is a reticulated product formed by a substantially continuous network of branching interconnected cellulose strands.

The bacterial cellulose prepared as above by the agitated fermentation has filament widths much smaller than softwood pulp fibers or cotton fiber. Typically these filaments will be about 0.05–0.20 μm in width with no definite length due to the continuous network structure. A softwood fiber averages about 30 μm in width and 2–5 mm in length while a cotton fiber is about half this width and about 25 mm long. The fine, fibrillar structure of the bacterial cellulose provides much more surface area in the wet state than other cellulose fibers. This results in high water holding capacity and suggests the potential for strong bonding.

By itself, when sheeted by conventional papermaking methods the bacterial cellulose tends to form sheets of relatively low density, very low porosity, and unusually high tensile index. (Tensile index is calculated by dividing tensile strength by grammage or basis weight.) However, the bacterial cellulose is a very slow draining material when used by itself.

When used as a minor component in admixture with other fibrous materials, bacterial cellulose made as described above conveys many of its desirable properties without seriously decreasing the drainage rate.

EXAMPLE 2

Effect of Sheet Density on Tensile Index of Bacterial Cellulose and Hemlock Kraft Sheets One characteristic of the bacterial cellulose used with the present invention is its excellent tensile strength even at very low sheet density. As was seen in the previous example, this characteristic is contributed to blends of bacterial cellulose with various wood pulps. Handsheets were made from all bacterial cellulose and all Douglas-fir kraft pulp over a range of densities. These handsheets were made to an approximate basis weight of 60 g/m² according to the procedure described in TAPPI official test method T205 om81. The bacterial cellulose (1.2 g in 2 L of water) was dispersed in a British disintegrator and sheeted on a 200 mesh wire screen in an automatic sheet mold. Drainage time exceeded 2 hours. The moist handsheets were initially gently pressed between blotters to remove excess water. Sheets were then placed in a TAPPI press between blotters under a 345 kPa load for varying times to produce sheets of various densities. Ultimately the sheets were dried using a conventional Noble and Wood drum dryer.

A Douglas-fir kraft pulp was similarly prepared and sheeted. However, this pulp was sheeted from unrefined stock and from samples refined in a PFI mill for 1500 and 7500 revolutions to achieve varying densities.

Figure 1:
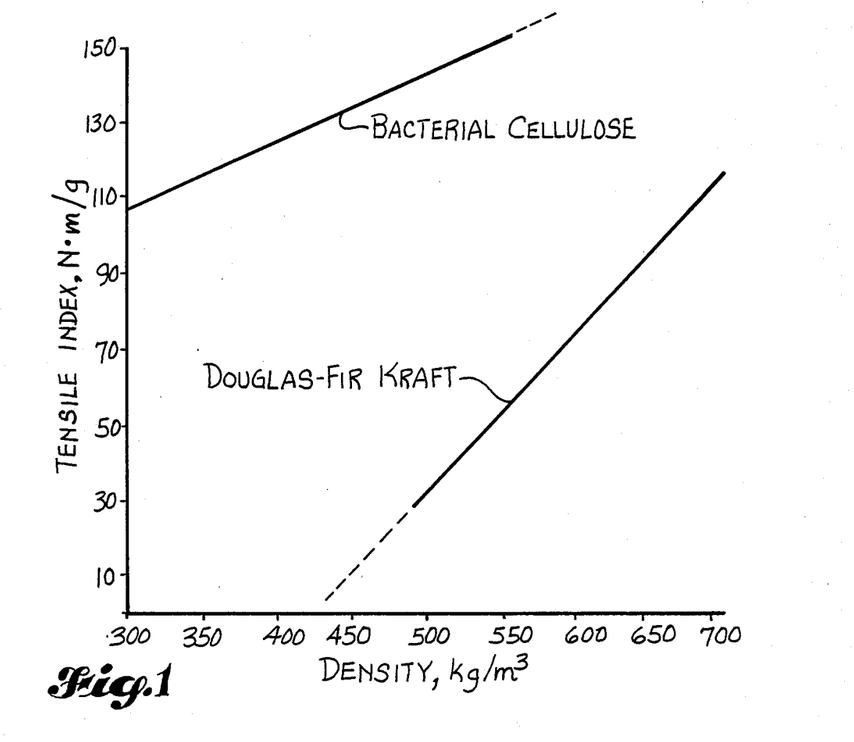
FIG. 1 is a comparison between an all bacterial cellulose product and a Douglas-fir pulp showing tensile index as a function of sheet density.

A comparison of tensile indices of bacterial cellulose and Douglas-fir kraft pulp at various sheet densities is shown in FIG. 1. Sheets made from bacterial cellulose have excellent tensile strength at very low sheet densities whereas the hemlock kraft sheets are very weak below densities of about 500 kg/m³.

EXAMPLE 3

Mixture of Bacterial Cellulose with Thermomechanical Wood Pulp

Kraft pulps are frequently added in minor percentages to thermomechanical pulps to enhance tensile and tear strengths. Bacterial cellulose (BAC) was further added to a mixture of thermomechanical (TM) newsprint pulp with 15% unrefined semibleached softwood kraft (SBK) pulp. The thermomechanical pulp was refined to a freeness of 74 CSF and the kraft pulp was at 659 CSF. Bacterial cellulose of the type described in Example 1 was used to replace thermomechanical pulp in amounts of 0, 1, 2 and 5%. Fiber slurries were prepared in a British Disintegrator and formed into Tappi standard handsheets using the procedure of Tappi method T205 om81. The resulting handsheets were conditioned and tested for tensile and tear strengths with the following results:

TABLE I

| Properties of TM Pulp/SBK Pulp/BAC Blends | | | | |
|---|---|---|---|---|
| TMP, % | SBK, % | BAC, % | Tensile Index, N°/g | Tear Index mN°m²/g |
| 100 | 0 | 0 | 38.2 | 7.1 |
| 85 | 15 | 0 | 38.2 | 10.1 |
| 84 | 15 | 1 | 41.9 | 10.4 |
| 83 | 15 | 2 | 44.4 | 10.3 |
| 80 | 15 | 5 | 46.1 | 9.5 |

The data show the very positive contribution of bacterial cellulose to tensile strength improvement without significantly penalizing tear strength.

EXAMPLE 4

Bacterial Cellulose Used in Nonwoven Fabrics

Bacterial cellulose contributes many desirable properties when used in place of or in conjunction with various resins as a bonding agent for nonwoven fabrics. Among the properties controlled are strength, porosity, hydrophilicity, and hand or feel of the product. Suitable fibers include all those currently used for nonwoven fabrics such as rayon, nylons, polyesters, polypropylene, and wood fibers. The material is expected to be useful also with glass and other inorganic fibers such as metal, carbon, etc.

It is most preferable that the nonwoven fabric be a wet-laid type since this process greatly simplifies uniform inclusion of the bacterial cellulose. Control of the formation process also permits the fabrics to be uniformly bonded or pattern bonded in a predetermined geometric form. Pattern bonding is useful to control drape and hand characteristics.

A series of samples was made using mixtures of polyester fiber and unrefined softwood kraft pulp fiber to simulate a nonwoven fabric typical of those used in surgical drapes and gowns. These fabrics are usually made from the following materials:

Polyester fibers (3 denier, 13 mm): 20–35%
Softwood kraft pulp fibers (unrefined): 30–50%
Hemp fibers: 0–5%
Soft acrylic latex binder: 20–30%
Fluorocarbon (water repellent): <1%

Polyester fibers of the above type were obtained from Mini Fibers, Inc., Johnson City, Tenn. as their product Code No. 6 3050. The softwood pulp was an undried, bleached Douglas-fir kraft pulp.

The bacterial cellulose and wood pulp (~0.9-1.2 g combined dry weight) were dispersed in a standard laboratory British disintegrator for 600 counts, or about 5 minutes (1 count is equal to 25 revolutions). Next, the polyester fiber and about 0.5 g of a nonionic surfactant (Triton X-100, Rohm and Haas Co., Philadelphia, Pa.) were added and dispersed for an additional 600 counts. The fiber slurry was sheeted in a Tappi sheet mold. Each sheet was drained, removed from the mold on the forming wire, covered with three blotter layers, couched with a standard Tappi roller, pressed 5 minutes at 345 kPa in a standard Tappi press, and dried on a drum dryer.

Samples were made with seven fiber combinations using levels of 0, 5, 10 and 20% bacterial cellulose. Compositions and pertinent physical properties are given in Table II.

TABLE II

Bacterial Cellulose Bonded Polyester Based Nonwoven Fabrics

| Polyester % | Wood Pulp % | BAC[1] % | Density kg/m³ | Tensile Index N°m/g | Stretch % | Tear Index mN°m²/g |
|---|---|---|---|---|---|---|
| 50 | 50 | 0 | 138 | 1.1 | 1.6 | 6.4 |
| 25 | 75 | 0 | 141 | 2.3 | 1.6 | 7.7 |
| 30 | 50 | 20 | 216 | 27.3 | 2.9 | 53.7 |
| 40 | 40 | 20 | 183 | 22.6 | 1.7 | >55 |
| 45 | 45 | 10 | 176 | 21.8 | 2.9 | >55 |
| 47.5 | 47.5 | 5 | 164 | 12.5 | 1.9 | 36.5 |
| 30 | 60 | 10 | 198 | 20.6 | 3.4 | 41.3 |
| 15 | 80 | 5 | 193 | 14.4 | 3.0 | 25.0 |
| 15 | 75 | 10 | 219 | 20.4 | 4.2 | 31.3 |
| 10 | 70 | 20 | 245 | 27.5 | 2.7 | 27.2 |
| 0 | 100 | 0 | 167 | 3.8 | 2.7 | 3.9 |

[1] Bacterial cellulose. All sheets were made at a basis weight of 60-61 g/m².

The use of even modest quantities of bacterial cellulose contributed significant tear and tensile strength to the fabric.

The efficiency of the bacterial cellulose as a binder can be seen by comparing the above samples with those conventionally bonded by a resin. Dried wet formed sheets using various blends of wood pulp and polyester fiber were conditioned for two hours at 50% R.H. and 20° C. These were placed on squares of polyethylene sheeting a sprayed with a sufficient amount of a resin emulsion (latex) to give the desired add-on. The latex used was a soft heat reactive acrylic material, Type 26120, supplied by B. F. Goodrich Co., Cleveland, Ohio, as a 48.5% solids emulsion. This was diluted to 6% solids content before spraying. One hour after spraying the wet sheets were placed on steel plates and stacked with brass drying rings to allow overnight air drying. The stacks of dried, latex treated sheets were then placed in an oven for 30 minutes at 150° C. to cure the latex. Sheets were conditioned and tested as above with the results being reported in Table III.

TABLE III

Latex Bonded Polyester Based Nonwoven Fabrics

| Polyester % | Wood Pulp % | BAC[1] % | Density kg/m³ | Tensile Index N°m/g | Stretch % | Tear Index mN°m²/g |
|---|---|---|---|---|---|---|
| 45 | 45 | 10 | 146 | 14.7 | 6.2 | >55 |
| 40 | 40 | 20 | 158 | 19.7 | 11.0 | >55 |
| 35 | 35 | 30 | 184 | 25.2 | 16.8 | >55 |
| 22.5 | 67.5 | 10 | 162 | 11.8 | 8.2 | 38.3 |
| 20 | 60 | 20 | 175 | 16.5 | 13.8 | 40.7 |
| 17.5 | 52.5 | 30 | 197 | 20.2 | 18.3 | 33.2 |

Figure 2:
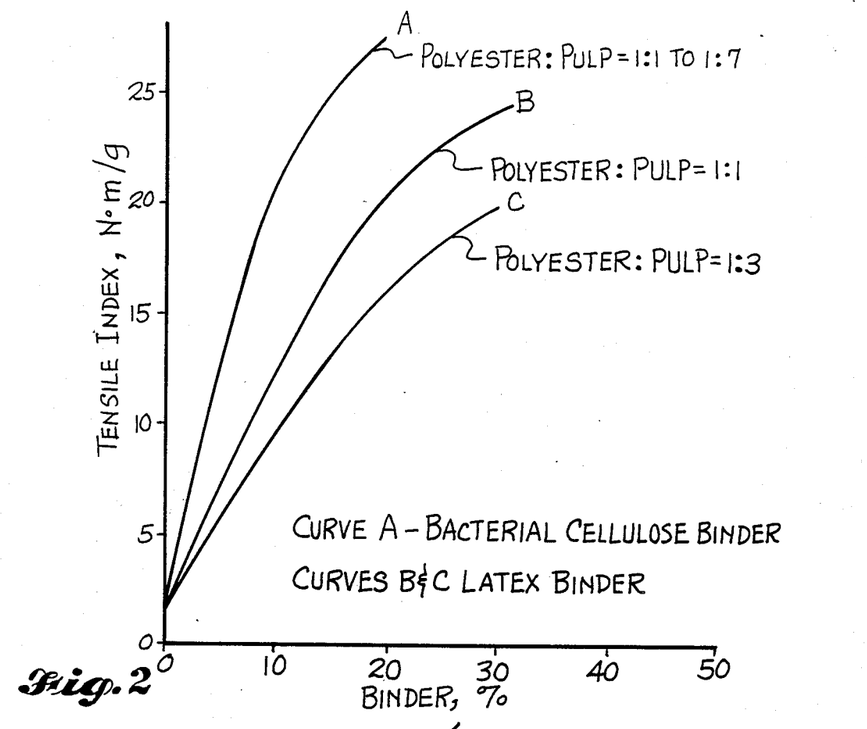
FIG. 2 is a plot of the effect of binder concentration on tensile index of various polyester fiber-wood pulp mixtures.

In general, bacterial cellulose is at least equivalent to the latex binder in contribution to tear strength. Bacterial cellulose is superior to the latex binder in all cases in its contribution to tensile strength. Further, tensile strength of the products made using the bacterial cellulose binder appears to be essentially insensitive to the ratio of polyester fiber to wood pulp. This is quite in contrast to the use of any given concentration of latex binder when tensile strength drops when the ratio of wood pulp to polyester is increased. This effect on tensile strength can be readily seen when the data of Tables II and III are plotted (FIG. 2). All of the points plotted for the bacterial cellulose binder fall closely on the upper curve, even over the wide ratios of polyester to wood pulp of 1:1 to 1:6.7. However, the two ratios of polyester to wood pulp used with latex binder fall on individual curves. This phenomenon is important because it indicates that much lower usages of the expensive polyester fiber would be acceptable using the bacterial cellulose binder. Expressed from the standpoint of binder efficiency 10% bacterial cellulose is equivalent in both tear and tensile strength contribution to 20-30% latex.

Further experiments have shown similar results to the above when all polyester fiber was used. It might be noted that the resin bonded materials are thus far superior to those bonded with bacterial cellulose when retention of tensile strength under wet conditions is a critical property.

EXAMPLE 5

Polypropylene and Polyester Sheets Bonded with Bacterial Cellulose

Separate blends of polypropylene and of polyester fibers were made using varying amounts of bacterial cellulose as a binder. These were prepared and formed into sheets in similar manner to the nonwoven fabrics described in Example 4. The polyester fibers were obtained from the supplier noted previously, but for this set of samples were a different length. They were 3 denier by 3.1 mm long and were identified as Code 6 31035. The polypropylene fiber was also supplied by Mini Fibers as Fibrel, Code E-990. These fibers were 1.2 denier by 2.5 mm long. No surfactant was needed to obtain good dispersion of either fiber.

Sheets were made with each synthetic fiber using 0, 2, 5, 10 and 20% bacterial cellulose. The polypropylene sheets having 20% bacterial cellulose stuck to the 200 mesh forming wire and were destroyed during removal. The remaining samples averaged between 60-61 g/m² basis weight. Polyester sheets made without any bacterial cellulose were so weak they could not be removed from the forming wire without tearing. The remaining samples averaged between 55-57 g/m² basis weight.

Figure 3:
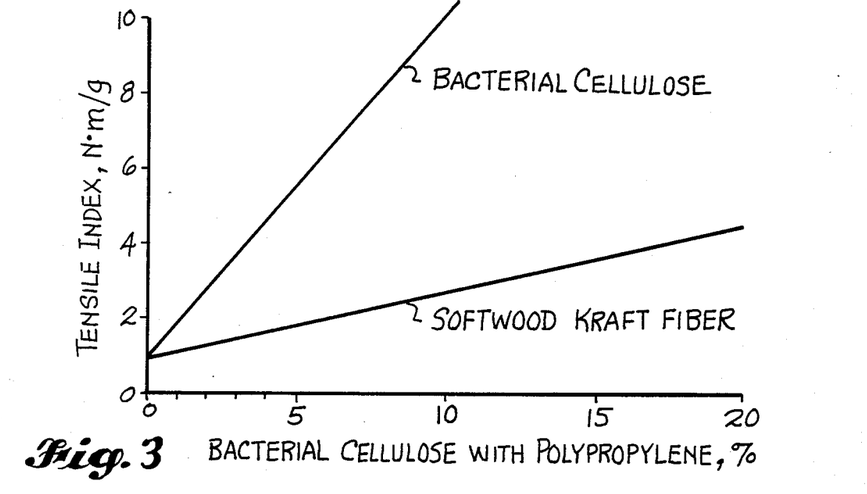
FIGS. 3–5 show improvements in tensile index when bacterial cellulose and softwood kraft fibers are added respectively to polypropylene, polyester and rayon fibers.
Figure 4:
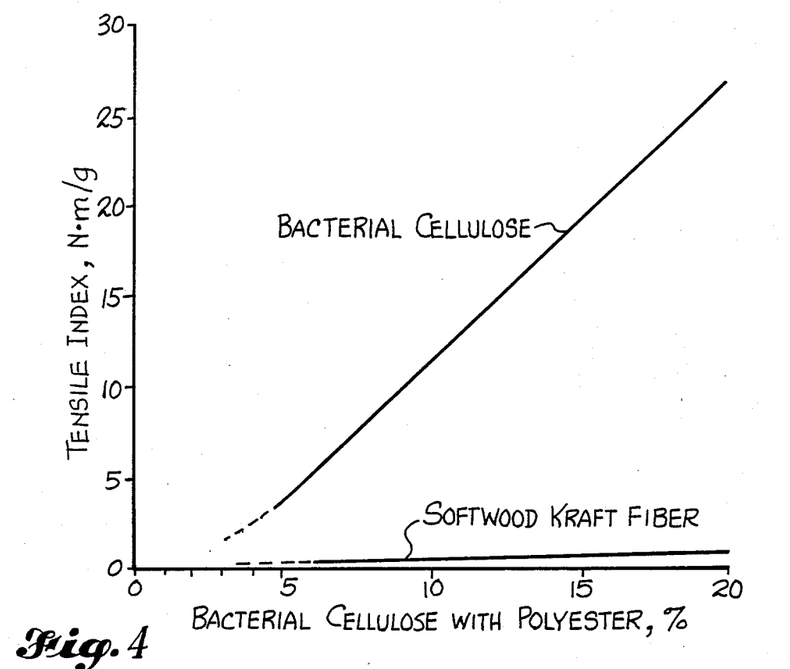

A duplicate set of sheets was also made using Douglas-fir kraft pulp beaten to a freeness of about 400 CSF in equivalent percentages as a replacement for bacterial cellulose. Tensile index was the property of greatest interest. These values are shown on FIG. 3 for the polypropylene samples and FIG. 4 for the polyester samples. The marked improvement in tensile index with addition of bacterial cellulose is immediately evident. This is especially dramatic with the polyester fiber.

EXAMPLE 6

Rayon Sheets Bonded with Bacterial Cellulose

Rayon fibers were used with a bacterial cellulose binder to make nonwoven sheets by a procedure similar to that of Examples 5 and 6. The rayon fibers were also 3 denier of 7 mm length and were obtained from the same supplier as the other fibers. Bacterial cellulose and Douglas-fir kraft pulp refined as before to a freeness of about 400 CSF were used in amounts of 5, 10 and 20%. Sheets were formed to a nominal 60 g/m² basis weight.

Figure 5:
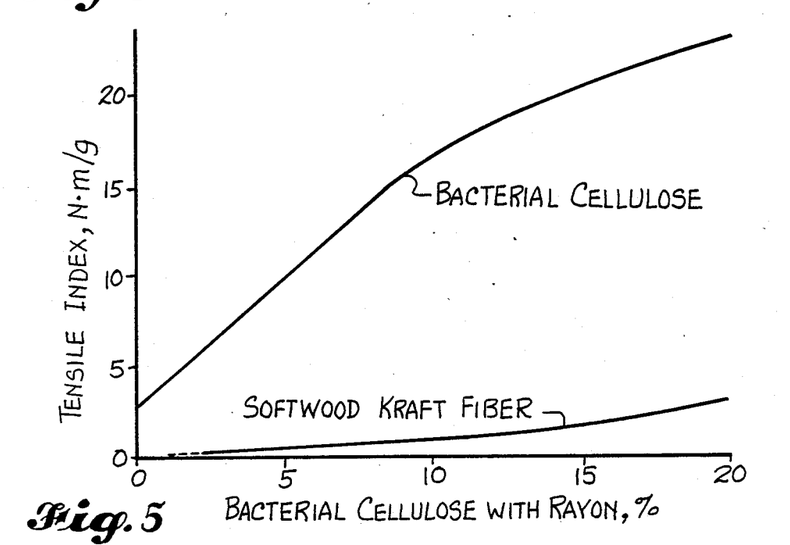

FIG. 5 shows results of tensile index tests on the above sheets. Once again, the effectiveness of bacterial cellulose as a binder is clearly shown.

EXAMPLE 7

Nonwoven Sheets Pattern Bonded with Bacterial Cellulose

Observations made on sheets of longer fibers blended with bacterial cellulose, formed on relatively large mesh screens, showed somewhat higher localized concentrations of the bacterial cellulose around the screen openings. This phenomenon suggested the possibility of a simple way of making pattern bonded fabrics using a bacterial cellulose binder. In a pattern bonded material the binder is applied in a predetermined geometric pattern rather than uniformly. This technique enables properties such as drape and hand to be modified according to the desired end use of the materials. In general, pattern bonded fabrics tend to be softer and have better drape than uniformly bonded types.

A mask was made of heavy aluminum foil for use over the 150 mesh forming screen in the sheet mold. This was patterned with 6 mm openings placed on a square grid with 12 mm centers. A 60 g/m² basis weight sheet was made using a furnish of 95% 12.5 mm, 3 denier, polyester fibers and 5% bacterial cellulose. The sheet was formed and dried as described in the earlier examples.

The resulting sheets were very attractive and had much better drape than conventionally formed sheets. Examination showed that the bacterial cellulose binder was concentrated over the areas of the drainage holes in the mask.

EXAMPLE 8

Effect of Creping on Sheets Bonded with Bacterial Cellulose

Another way of modifying hand and drape properties of nonwoven fabrics is by creping. A number of creping processes are available. The one used in this example was the Micrex process, a proprietary process of Bird Machine Company, Walpole, Mass.

A number of samples of polyester and softwood kraft fibers were made as described in Example 5. Some were bonded with bacterial cellulose and others with latex. A portion of the resulting sheets were then creped by the Micrex process. These were then compared with their uncreped counterparts for tear index, tensile index, and drape. All samples were in the 60–61 g/m² basis weight range. Drape is determined by cantilevering a 150 mm diameter circular sheet over the edge of a block 24 mm above a table surface and measuring the distance from the block when the end of the sample first touches the table. All samples were measured felt side up and those that were creped were oriented with the creping direction parallel to the edge of the block. Fabric compositions and the results of tests are given in Table IV.

TABLE IV

| Composition | | | | Results of Creping Nonwoven Fabrics | | | | | |
|---|---|---|---|---|---|---|---|---|---|
| | | | | Tear Index mN·m²/g | | Tensile Index N·m/g | | Drape mm | |
| PE % | Pulp % | BAC % | Latex % | Original | Creped | Original | Creped | Original | Creped |
| 40 | 40 | 20 | — | 54.7 | 79.1 | 33.9 | 33.7 | 120 | 56 |
| 45 | 45 | 10 | — | 58.0 | 39.1 | 22.4 | 13.9 | 130 | 40 |
| 47.5 | 47.5 | 5 | — | 23.0 | 24.5 | 6.4 | 8.9 | 128 | 37 |
| 30 | 60 | 10 | — | 41.9 | 32.3 | 26.2 | 17.2 | 112 | 40 |
| 15 | 75 | 10 | — | 27.1 | 27.3 | 22.5 | 20.8 | 93 | 38 |
| 10 | 80 | 10 | — | 23.0 | 22.9 | 28.0 | 21.3 | 86 | 47 |
| 33 | 33 | — | 33 | 49.3 | 67.8 | 25.4 | 32.8 | 110 | 45 |
| 17.5 | 52.5 | — | 30 | 33.8 | 43.7 | 28.0 | 35.5 | 100 | 45 |

The effect of creping had variable effect on tensile and tear indices. These were increased in both cases for the latex bonded pulps while the bacterial cellulose bonded pulps were, on the average, generally unaffected. Drape length was decreased slightly more for the bacterial cellulose bonded fabrics than for the latex bonded materials.

EXAMPLE 9

Bacterial Cellulose Compared with Highly Beaten Wood Pulp

As has been noted before, the bacterial cellulose used in the present invention is a highly hydrophilic material. As a result of this high water affinity, slurries of the material drain very slowly. In this regard the bacterial cellulose has some resemblance to very highly beaten, or so-called "dead beaten" wood pulps. There are very significant differences, however. Bacterial cellulose sheets tend to have similar physical properties to highly beaten wood pulp sheets as far as tensile and burst indices are concerned. Air porosity of the bacterial cellulose sheets is at least a full order of magnitude lower than the wood pulp sheets at similar sheet densities. This is shown in the following tables:

TABLE V

| Bacterial Cellulose vs. Highly Beaten Kraft Pulp[1] | | | | | | |
|---|---|---|---|---|---|---|
| Sample | Freeness C.S.F. | Sheet Density kg/m³ | Tensile Index N·m/g | M.O.E. GPa | Stretch, % | Burst Index kN/g |
| Bacterial | — | 373 | 132.0 | 4.61 | 2.3 | 8.1 |
| Bacterial | — | 463 | 84.0 | 3.56 | 1.9 | 5.2 |
| Bacterial | — | 555 | 88.9 | 4.31 | 1.9 | 4.4 |
| Softwood | 75 | 486 | 59.0 | 2.07 | 4.0 | 6.4 |

TABLE V-continued

Bacterial Cellulose vs. Highly Beaten Kraft Pulp[1]

| Sample | Freeness C.S.F. | Sheet Density kg/m³ | Tensile Index N°m/g | M.O.E. GPa | Stretch. % | Burst Index kN/g |
|---|---|---|---|---|---|---|
| kraft Softwood kraft | 45 | 516 | 75.8 | 2.94 | 2.5 | 7.5 |

[1] All sheets were nominal 60 g/m² basis weight.

TABLE VI

Bacterial Cellulose vs. Highly Beaten Sulfite Pulp[1]

| Sample | Density kg/m³ | Tensile Index N°m/g | Wet Tensile Index N°m/g | Stretch % | Burst Index kN/g | Porosity sec/100 mL |
|---|---|---|---|---|---|---|
| Bacterial | 359 | 73.8 | 1.5 | 2.4 | 2.7 | — |
| Bacterial | 454 | — | — | — | — | 37,800 |
| Bacterial | 503 | 119.1 | 1.3 | 1.5 | 4.5 | >6,000 |
| Softwood sulfite[2] | 598 | 54.2 | 1.6 | 2.8 | 3.1 | 112 |
| Softwood sulfite | 670 | 60.6 | 1.9 | 2.7 | 3.4 | 372 |
| Softwood sulfite | 711 | 61.2 | 2.1 | 3.2 | 3.8 | 67.2 |

[1] All sheets were a nominal 60 g/m² basis weight.
[2] All sulfite pulps were beaten to a freeness of 55 mL C.S.F.

Highly beaten softwood kraft pulp is much less effective than bacterial cellulose as a binder for nonwoven fiber sheets. Bacterial cellulose gives significantly higher tensile strengths than does highly beaten pulp.

A comparison was made using both polyester and polypropylene fibers with bacterial cellulose and softwood kraft pulp refined to a freeness of 45 C.S.F. Physical properties of the resulting fiber blends are shown in Table VII.

TABLE VIII

Bacterial Cellulose vs. Highly Beaten Pulp as Nonwoven Binder

| Fiber Type | Ratio, Fiber/ BAC | Ratio, Fiber/ Wood Pulp[1] | Basis Weight g/m² | Density kg/m³ | Tensile Index N°m/g | Burst Index kN/g |
|---|---|---|---|---|---|---|
| Polypropylene | 95/5 | — | 59.9 | 244 | 6.5 | 0.67 |
| Polypropylene | — | 95/5 | 64.3 | 228 | 2.9 | 0.34 |
| Polyester | 90/10 | — | 56.5 | 192 | 12.1 | — |
| Polyester | — | 90/10 | 45.7 | 158 | 0.6 | 0.42 |

[1] Softwood kraft pulp beaten to a freshness of 45 C.S.F.

It will be obvious to those skilled in the art that many departures can be made from the examples just given without departing from the spirit of the invention. Many other types, lengths, weights, etc. of fibrous materials beyond those described in the examples are suitable. Various blends of fibers are equally suitable. Bacterial cellulose may be advantageously used in conjunction with a latex binder in some instances. In this regard, the only criterion that should be met is that the bacterial cellulose should be a minor portion by weight of the dry components. Normally the bacterial cellulose should not exceed 30%, more preferably about 20%, of the total dry weight of the furnish.

We claim:

1. A method of bonding a fibrous wet laid nonwoven paper or fabric-like product which comprises adding to the fibers thereof as a binder prior to wet forming the product a minor portion of an aqueous dispersion of a bacterial cellulose essentially free of bacterial cells, said bacterial cellulose having a reticulated structure formed by a substantially continuous network of branching interconnected cellulose strands, said bacterial cellulose being produced by a microorganism of the genus Acetobacter cultured under agitated aerobic conditions, said microorganism being selected from a stable strain resistant to mutation to non-cellulose producing types under said culturing conditions.

2. The method of claim 1 in which the bacterial cellulose binder is present in an amount of 1–30% by weight of the product.

3. The method of claim 2 in which the bacterial cellulose binder is present in an amount of 2–20% by weight of the product.

4. The method of claim 1 in which the fibers are selected from the group consisting of cellulose, polyester, polyolefin, nylon, acrylic, glass, and metal fibers.

5. The method of claim 4 in which the major portion of the fibers are polyester.

6. The method of claim 4 in which the major portion of the fibers are polyolefin.

7. The method of claim 6 in which the major portion of the fibers are polypropylene.

8. The method of claim 4 in which the major portion of the fibers are rayon.

9. The method of claim 4 in which the major portion of the fibers are wood pulp fibers.

10. The method of claim 1 which further includes wet forming the product over a mask-like drainage means to produce a pattern bonded material.

11. A nonwoven paper or fabric-like product comprising a major portion of a fibrous substrate forming material and a minor portion of a bacterial cellulose essentially free of bacterial cells serving as a binder for the fibrous material, said bacterial cellulose being produced by a microorganism of the genus Acetobacter cultured under agitated aerobic conditions and having a reticulated structure formed by a substantially continuous network of branching interconnected cellulose strands, said microorganism being selected from a stable strain resistant to mutation to non-cellulose producing types under said culturing conditions.

12. The product of claim 11 in which the bacterial cellulose binder is present in an amount of 1–30% by weight of the product.

13. The product of claim 12 in which the bacterial cellulose binder is present in an amount of 2-20% by weight of the product.

14. The product of claim 11 in which the fiber in the substrate forming material is selected from the group consisting of cellulose, polyester, polyolefin, nylon, acrylic, glass, and metal fibers.

15. The product of claim 14 in which the major portion of the fibers are polyester.

16. The product of claim 14 in which the major portion of the fibers are polyolefin.

17. The product of claim 16 in which the major portion of the fibers are polypropylene.

18. The product of claim 14 in which the major portion of the fibers are rayon.

19. The product of claim 14 in which the major portion of the fibers are wood pulp fibers.

20. The product of claim 11 which is pattern bonded in localized areas by the bacterial cellulose.

* * * * *